(12) United States Patent
Weidenhaupt et al.

(10) Patent No.: US 9,376,551 B2
(45) Date of Patent: Jun. 28, 2016

(54) CROSS-LINKED ORGANOSILICON POLYSULFIDES

(75) Inventors: Hermann-Josef Weidenhaupt, Pulheim (DE); Melanie Wiedemeier-Jarad, Dormagen (DE); Ulrich Feldhues, Bergisch Gladbach (DE)

(73) Assignee: LANXESS Deutschland GmbH, Cologne (DE)

( * ) Notice: Subject to any disclaimer, the term of this patent is extended or adjusted under 35 U.S.C. 154(b) by 0 days.

(21) Appl. No.: 14/237,580

(22) PCT Filed: Aug. 9, 2012

(86) PCT No.: PCT/EP2012/065560
§ 371 (c)(1),
(2), (4) Date: Aug. 6, 2014

(87) PCT Pub. No.: WO2013/023978
PCT Pub. Date: Feb. 21, 2013

(65) Prior Publication Data
US 2014/0350158 A1    Nov. 27, 2014

(30) Foreign Application Priority Data
Aug. 12, 2011 (EP) .................................... 11177443

(51) Int. Cl.
| | |
|---|---|
| *C08K 5/548* | (2006.01) |
| *C07F 7/08* | (2006.01) |
| *C07F 7/18* | (2006.01) |
| *C08L 7/00* | (2006.01) |
| *C08L 9/06* | (2006.01) |

(52) U.S. Cl.
CPC ............... *C08K 5/548* (2013.01); *C07F 7/0856* (2013.01); *C07F 7/1836* (2013.01); *C07F 7/1892* (2013.01); *C08L 7/00* (2013.01); *C08L 9/06* (2013.01)

(58) Field of Classification Search
CPC .... C07F 7/0856; C07F 7/1836; C07F 7/1892; C08K 5/548
See application file for complete search history.

(56) References Cited

U.S. PATENT DOCUMENTS

| | | |
|---|---|---|
| 4,076,550 A | 2/1978 | Thurn et al. |
| 4,709,065 A | 11/1987 | Yoshioka et al. |
| 5,107,009 A | 4/1992 | Rauleder et al. |
| 5,110,969 A | 5/1992 | Dittrich et al. |
| 5,663,226 A | 9/1997 | Scholl et al. |
| 5,827,912 A | 10/1998 | Scholl |
| 5,977,225 A | 11/1999 | Scholl et al. |
| 6,268,421 B1 | 7/2001 | Dittrich et al. |
| 6,359,045 B1 | 3/2002 | Jeske et al. |
| 6,689,834 B2 | 2/2004 | Ackermann et al. |
| 8,193,265 B2 | 6/2012 | Nakayama et al. |
| 8,288,474 B2 | 10/2012 | Hergenrother et al. |
| 2011/0098389 A1* | 4/2011 | Yoo et al. ...................... 524/261 |

FOREIGN PATENT DOCUMENTS

| | | |
|---|---|---|
| EP | 1514898 A1 | 3/2005 |
| GB | 1102251 | 2/1968 |
| JP | 2010-241723 A | 10/2010 |
| JP | 2010-248155 A | 11/2010 |
| JP | 2011-122128 | 6/2011 |
| WO | 2004000930 A1 | 12/2003 |
| WO | 2009142222 A1 | 11/2009 |

OTHER PUBLICATIONS

Murinov, Yuri, et al., "Reaction ability of heterochain complex-forming organopolymeric and organosilicon S-, N-containing sorbents toward noble metals", published on the web May 9, 2002, ARKIVOC 2001 (ix), ARKAT USA, Inc. pp. 166-186.
Vlasova, N., et al., "Hydrolytic condensation of bis [S, S-(2-triethoxysilylethyl) ethylene disulfide]", Zhurnal Obshchei Khimii (1996), 66 (12), 1952-1954, Nauka, Moscow, Russia, Caplus record.
European Search Report from co-pending European application No. EP19960108899, dated Oct. 1, 1996, 1 page.

\* cited by examiner

*Primary Examiner* — Margaret Moore

(57) ABSTRACT

The present invention relates to new crosslinked organosilicon polysulphides, to processes for preparing them and to their use as additives for plastics and/or rubbers.

19 Claims, 1 Drawing Sheet

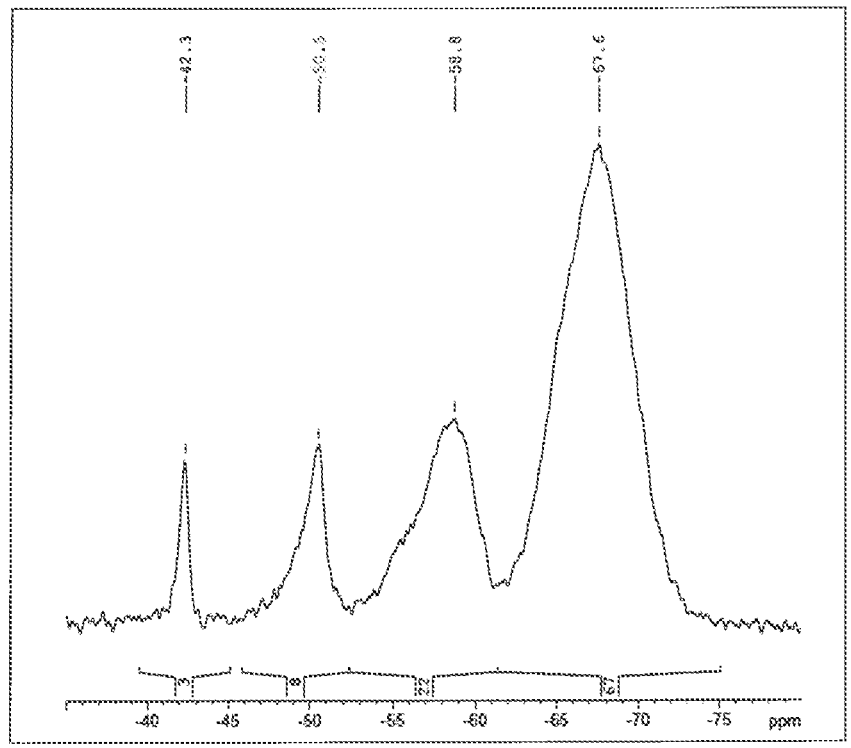

CROSS-LINKED ORGANOSILICON POLYSULFIDES

The invention relates to new crosslinked organosilicon polysulphides, to processes for preparing them and to their use as additives for plastics and/or rubbers.

20 to 25 percent of the fuel consumption of a car results from the rolling resistance of the tyres; in the case of lorries, the figure is in fact around 30 percent.

These values caused the EU Commission to oblige the automobile industry by ordinance to use low-rolling-resistance tyres. For new vehicles the obligation enters into force in 2011. By far the greater part of the market, however, is made up of tyres which are used as replacements for their old and worn-out counterparts. From 2012 onwards, these tyres must be labelled in respect of their fuel efficiency, wet grip and rolling noise. Similarly to the system already known for household appliances, classes from A (best performance) to G (worst performance) are intended to bring about more transparency for the consumer and to aid him or her in decision-making when purchasing new tyres.

For some time, and certainly since the European Union addressed the limits for the output of carbon dioxide by cars, the car manufacturers have been looking for financially viable ways to achieve the target $CO_2$ emission mark of not more than 130 g/km. Key importance here is accorded to low-rolling-resistance tyres. They perform less deformation work when rolling and therefore lower the fuel consumption.

In order that the reduction in rolling resistance is not acquired at the expense of other important properties, the requirements for wet grip and rolling noise are stipulated at the same time. An initial indication of wet slip behaviour and rolling resistance is provided by the loss factor tan $\delta$. This factor ought to be as high as possible at 0° C. (good wet grip) and as low as possible at 60 to 70° C. (reduction in rolling resistance).

There is therefore a great demand for improved rubber mixtures which when used in tyre making lead to products possessing enhanced properties, such as lower rolling resistance and rolling noise and better wet grip.

A series of proposed solutions have already been developed for the production of tyres featuring reduced rolling resistance. DE-A 2 255 577, DE-A 4 435 311, EP-A 0670 347 and U.S. Pat. No. 4,709,065 had described certain polysulphidic silanes as reinforcing additives for silica-containing rubber vulcanizates. These reinforcing additives, however, are still in need of improvement. A disadvantage when using these known additives, for example, is that relatively large quantities of the expensive polysulphidic silanes must be used in order to achieve acceptable processing properties.

Sulphur-containing organosilicon compounds are already known from the prior art.

Thus, for example, EP-A 670347 and EP-A 748839 describe sulphur-containing and silicon-containing compounds as reinforcing additives in rubber mixtures.

EP-A 864608 discloses the use of polysulphidic polyethersilanes in rubber mixtures.

The known sulphur-containing organosilicon compounds are used as reinforcing additives in rubber mixtures and are intended to enhance the properties of the rubber vulcanizates produced therewith. More recently, efforts have been directed particularly at finding additives which when used in tyre-making lead to products which possess enhanced properties, such as lower rolling resistance, low rolling noise and better wet grip. The presently known additives based on sulphur-containing organosilicon compounds are, however, still in need of improvement in this respect.

It was an object of the present invention to provide a new, improved additive for plastics and/or rubbers that positively modifies the adhesion, crosslinking and surface quality of the plastics and/or rubbers.

New, crosslinked organosilicon polysulphides have been found which are outstandingly suitable as additives for plastics and/or rubbers, more particularly as adhesion promoters, crosslinking agents and surface modifiers. Especially when used in silica-containing rubber mixtures, the use of the crosslinked organosilicon polysulphides of the invention as reinforcing additives leads to improved properties in the vulcanizates produced therefrom, in respect, for example, of the rolling resistance of vehicle tyres.

The present invention provides compounds of the formula

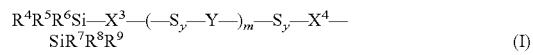

in which $X^3$ and $X^4$ independently of one another are alkylene,

Y is a divalent, optionally substituted, optionally heteroatom-containing aliphatic, cycloaliphatic or aromatic group, y is an integer from 1 to 6, m is an integer from 0 to 20 and $R^4$, $R^5$, $R^6$, $R^7$, $R^8$ and $R^9$ independently of one another are —OH, —Ometal, alkyl, alkoxy, phenyl or phenoxy, and at least one of the substituents $R^4$, $R^5$, $R^6$, $R^7$, $R^8$ and $R^9$ is a radical of the formula

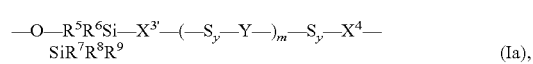

where the substituents and indices in the formula (Ia) have the definition stated above for formula (I), metal is a metal ion from the series of the alkali metals and alkaline earth metals, and optionally the radicals of the formula (Ia) are joined via one or more —Si—O—Si— units to further radicals of the formula (Ia).

Preference is given to compounds of the formula (I), in which $X^3$ and $X^4$ independently of one another are $C_1$-$C_6$-alkylene, Y is a straight-chain, branched or cyclic $C_4$-$C_{18}$-alkylene radical which is optionally substituted by $C_6$-$C_{12}$-aryl, $C_1$-$C_8$-alkoxy or hydroxyl groups and which is optionally interrupted by oxygen, sulphur or nitrogen atoms or by $C_6$-$C_{12}$-aryl, or is a divalent, optionally substituted, optionally heteroatom-containing aliphatic, cycloaliphatic or aromatic group, y is an integer from 2 to 4, m is an integer from 0 to 6 and $R^4$, $R^5$, $R^6$, $R^7$, $R^8$ and $R^9$ independently of one another are —OH, —Ometal, or $C_1$-$C_8$-alkoxy, and at least one of the substituents $R^4$, $R^5$, $R^6$, $R^7$, $R^8$ and $R^9$ is a radical of the formula

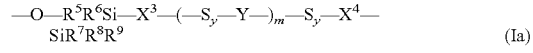

where the substituents and indices in formula (Ia) have the definition stated above for formula (I), metal is a metal ion selected from the series Na, K, Mg/2 and Ca/2, and optionally the radicals of the formula (Ia) are joined via one or more —Si—O—Si— units to further radicals of the formula (Ia).

Particular preference is given to compounds of the above-stated formulae (I),
in which
$X^3$ and $X^4$ independently of one another are $C_2$-$C_3$-alkylene,
Y is a radical of the formula —(—CH$_2$—)$_a$— where a=2-12
or

—CH$_2$CH$_2$—(—OCH$_2$CH$_2$—)$_b$— where b=1-4
y is an integer from 2 to 4,
m is 0, 1, 2, 3, 4, 5 or 6,
$R^4$, $R^5$, $R^6$, $R^7$, $R^8$ and $R^9$ independently of one another are —OH, —ONa, —OK, —O—(Mg/2), —O—(Ca/2), methoxy or ethoxy,
and
at least one of the substituents $R^4$, $R^5$, $R^6$, $R^7$, $R^8$ and $R^9$ is a radical of the formula —O—R$^5$R$^6$Si—X$^3$—(—S$_y$—Y—)$_m$—S$_y$—X$^4$— (Ia)
SiR$^7$R$^8$R$^9$ where the substituents and indices in formula (Ia) have the definitions stated above for formula (I),
and optionally the radicals of the formula (Ia) are joined via one or more —Si—O—Si— units to further radicals of the formula (Ia).
Very particular preference is given to compounds of the above-stated formula (I), in which
$X^3$ and $X^4$ independently of one another are $C_2$-$C_3$-alkylene,
Y is —(CH$_2$)—$_6$
y is 2, 3 or 4,
m is 1,
$R^4$, $R^5$, $R^6$, $R^7$, $R^8$ and $R^9$ independently of one another are —OH, —ONa, methoxy or ethoxy and
at least one of the substituents $R^4$, $R^5$, $R^6$, $R^7$, $R^8$ and $R^9$ is a radical of the formula —O—R$^5$R$^6$Si—X$^3$—(—S$_y$—Y—)$_m$—S$_y$—X$^4$— (Ia)
SiR$^7$R$^8$R$^9$ where the substituents and indices in formula (Ia) have the definitions stated above for formula (I),
and optionally the radicals of the formula (Ia) are joined via one or more —Si—O—Si— units to further radicals of the formula (Ia).

Further very particular preference is given to compounds of the above-stated formula (I), in which
$X^3$ and $X^4$ independently of one another are $C_2$-$C_3$-alkylene,
y is 2, 3 or 4,
m is 0,
$R^4$, $R^5$, $R^6$, $R^7$, $R^8$ and $R^9$ independently of one another are —OH, —ONa, methoxy or ethoxy and
at least one of the substituents $R^4$, $R^5$, $R^6$, $R^7$, $R^8$ and $R^9$ is a radical of the formula —O—R$^5$R$^6$Si—X$^3$—(—S$_y$—Y—)$_m$—S$_y$—X$^4$— (Ia)
SiR$^7$R$^8$R$^9$ where the substituents and indices in formula (Ia) have the definitions stated above for formula (I),
and optionally the radicals of the formula (Ia) are joined via one or more —Si—O—Si— units to further radicals of the formula (Ia).

The compounds of the formula (I) take the form of crosslinked structures. The compounds of the formula (I) are preferably crosslinked organosilicon polysulphides which are joined via at least one Si—O—Si unit. Preferably at least 50 percent of the Si atoms present are joined via at least one Si—O—Si unit. More preferably at least 50% of the Si atoms in the compounds of the formula (I) are crosslinked via at least one —Si(OSi—)$_2$— and very preferably via at least one —Si(OSi—)$_3$— unit.

The compounds of the formula (I) contain in general
0% to 100% by weight of structural units of the formula —Si(OSi)$_3$
0% to 50% by weight of structural units of the formula —Si(OSi)$_2$(OR)$_1$
0% to 50% by weight of structural units of the formula —Si(OSi)$_1$(OR)$_2$
0% to 100% by weight of structural units of the formula —Si(OR)$_3$
where R in particular is H, methyl and/or ethyl and the % by weight add up to 100 percent.

The structures below are intended to illustrate by way of example how the environment of an Si atom in an organosilicon polysulphide of the invention (here the silicon atom marked in bold) may look, depending on the degree of crosslinking, without restricting the invention thereto.

Illustration for a structural unit of the formula —Si(OR)$_3$ with R=ethyl:

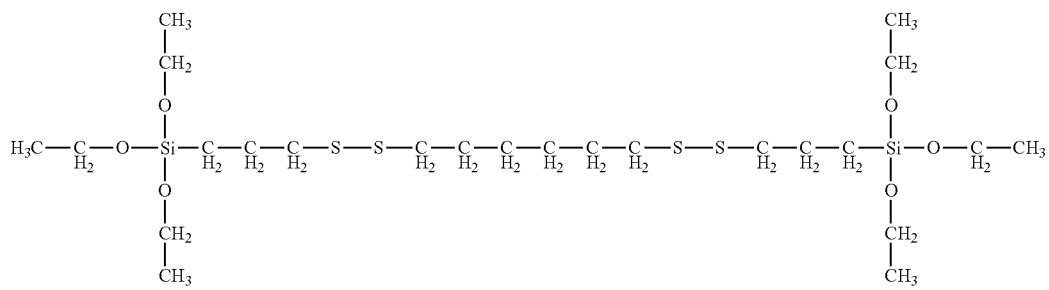

Illustration for a structural unit of the formula —Si(OSi)$_1$(OR)$_2$ with R=ethyl:
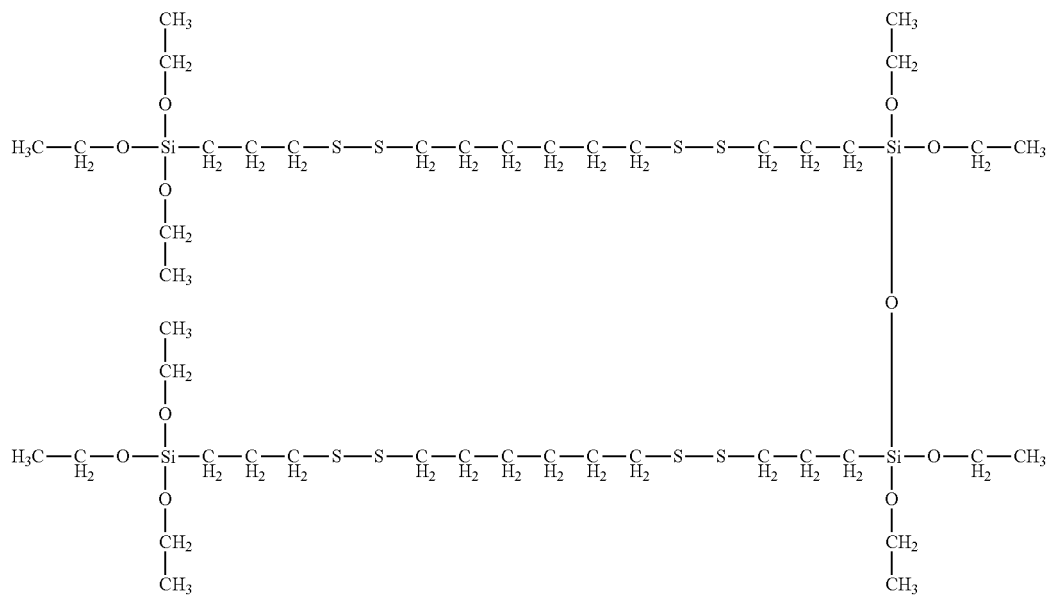
Illustration for a structural unit of the formula —Si(OSi)$_2$(OR)$_1$ with R=ethyl:
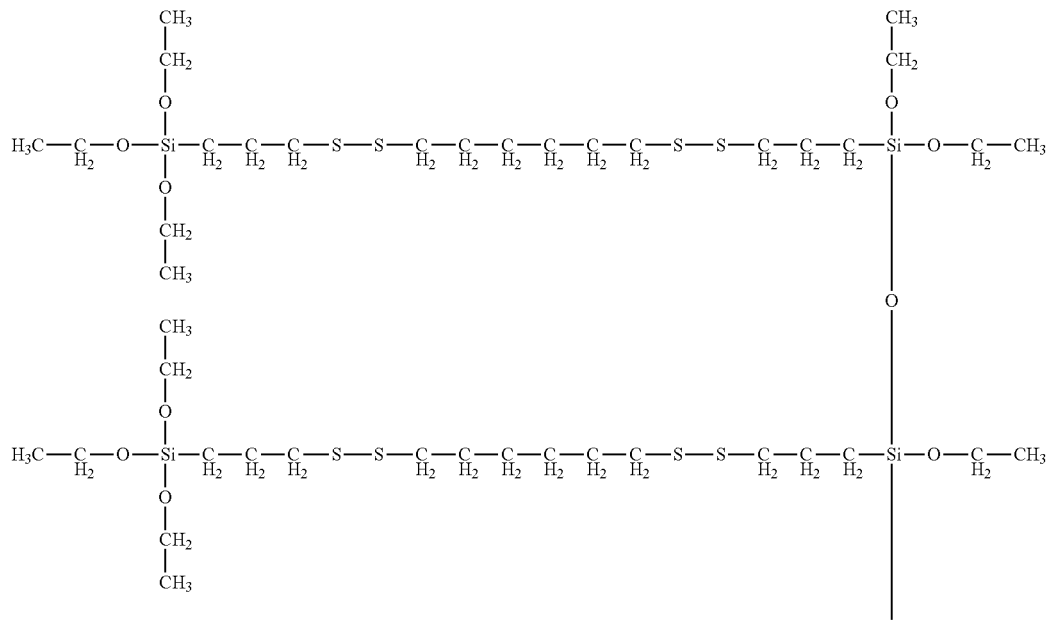

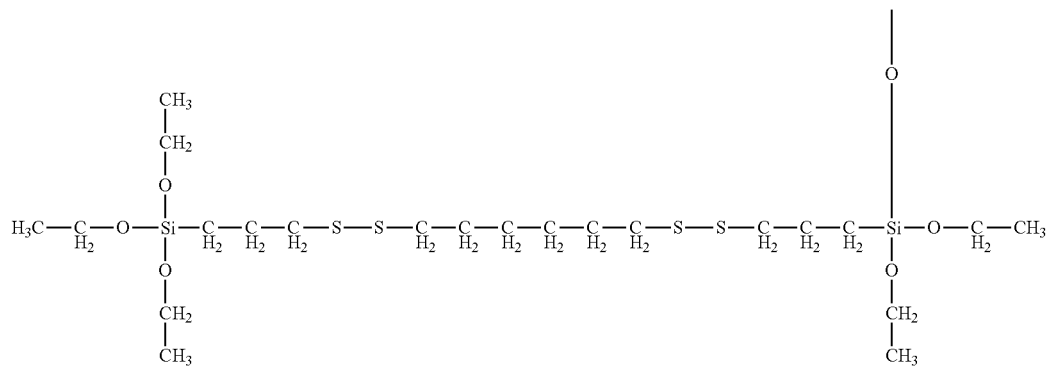
Illustration for a structural unit of the formula —Si(OSi)$_3$:
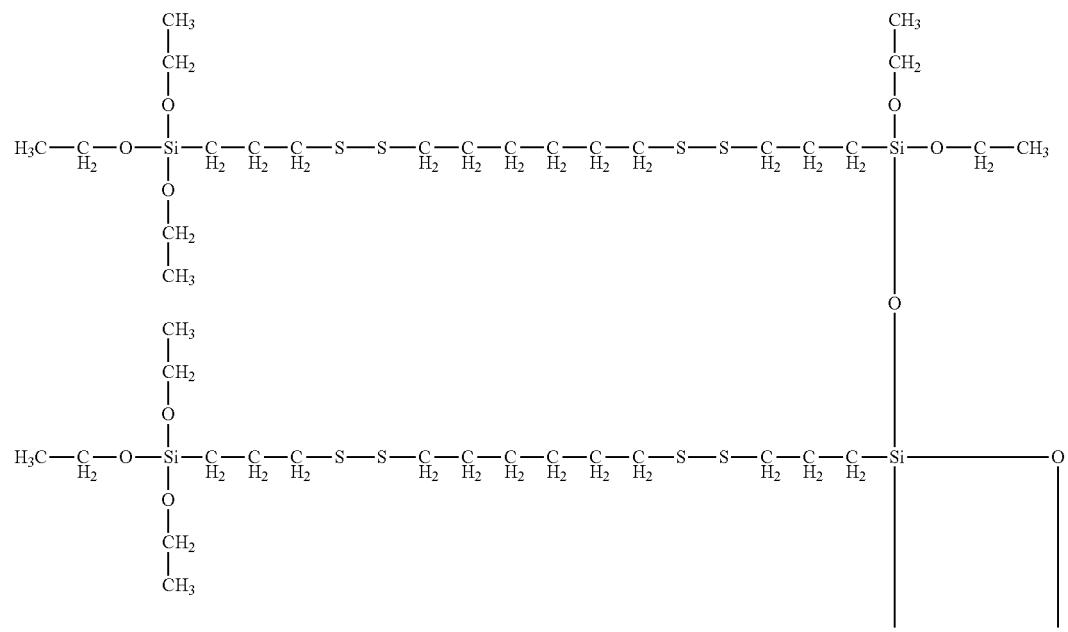

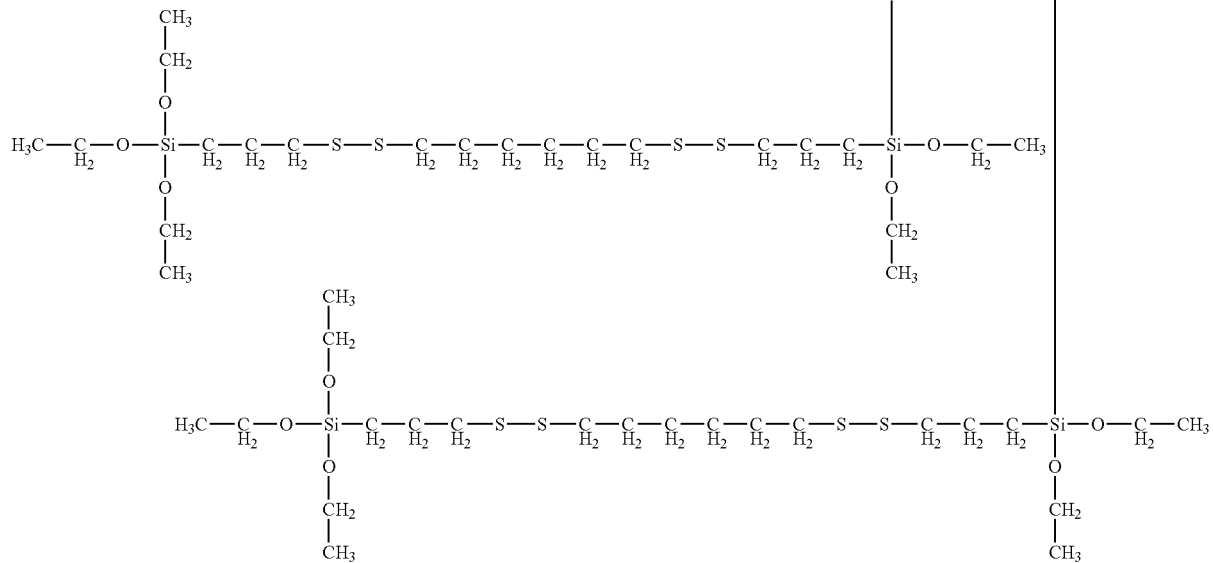

The compounds of the formula (I) contain preferably

0% to 100% by weight of structural units of the formula —Si(OSi)$_3$

0% to 50% by weight of structural units of the formula —Si(OSi)$_2$(OR)$_1$

0% to 30% by weight of structural units of the formula —Si(OSi)$_1$(OR)$_2$

0% to 20% by weight of structural units of the formula —Si(OR)$_3$ where R in particular is H, methyl and/or ethyl and the % by weight add up to 100 percent.

The above-stated weight percentages relate in each case to 100% by weight of compound of the formula (I).

Especially preferred are those compounds of the formula (I), in which

X$^3$ and X$^4$ independently of one another are C$_2$-C$_3$-alkylene,

Y is —(CH$_2$)—$_6$, y is an integer from 2 to 4, m is 1,

R$^4$, R$^5$, R$^6$, R$^7$, R$^8$ and R$^9$ independently of one another are —OH, —ONa, methoxy or ethoxy, and at least one, preferably two or more, of the radicals R$^4$, R$^5$, R$^6$, R$^7$, R$^8$ and R$^9$ are a radical of the formula

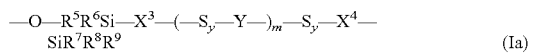

(Ia)

in which the substituents and indices in formula (Ia) have the definitions stated above for formula (I), and optionally the radicals of the formula (Ia) are joined via one or more —Si—O—Si— units to further radicals of the formula (Ia), and the compound of the formula (I) comprises 0% to 100% by weight, preferably 40-90% by weight and more particularly 50-80% by weight of structural units of the formula —Si(OSi)$_3$ 0% to 50% by weight, preferably 10-40% by weight and more particularly 10-30% by weight of structural units of the formula —Si(OSi)$_2$(OR)$_1$ 0% to 30% by weight, preferably 0-20% by weight and more particularly 5-15% by weight of structural units of the formula —Si(OSi)$_1$(OR)$_2$ 0% to 20% by weight, preferably 0-10% by weight, and more particularly 0-5% by weight of structural units of the formula —Si(OR)$_3$, where R is H, Na, methyl and/or ethyl.

It has now been found that the crosslinked organosilicon polysulphides of the formula (I) of the invention are outstandingly suitable as additives for plastics and/or rubbers, more particularly as adhesion promoters, crosslinking agents and surface modifiers.

The present invention also provides for the use of the crosslinked organosilicon polysulphides of the formula (I) of the invention as additives for plastics and/or rubbers.

It is known that the use of standard commercial alkoxysilane compounds as coupling reagents during and after attachment to the filler leads to the release of considerable amounts of alcohol. Since the silanes used are generally trimethoxy- and triethoxy-substituted, the corresponding alcohols, methanol and ethanol, are released in considerable quantities. From a technical standpoint, however, it has not been possible to forgo the use of methoxy- and ethoxy-substituted silanes, since they possess a high reactivity and are therefore able to attach quickly to the surface—the filler, for example—for coupling/crosslinking.

The crosslinked organosilicon polysulphides of the formula (I) of the invention are distinguished by low volatility and during attachment to the filler release little or no alcohol and surprisingly, in spite of their crosslinking, exhibit a high level of reactivity with respect to the surface for coupling/crosslinking.

The additive of the invention can be used as an adhesion promoter between inorganic materials, for example glass fibres, metals, oxidic fillers, silicas and organic polymers, for example thermosets, thermoplastics or elastomers, and/or as a crosslinking agent and surface modifier.

The compounds of the formula (I) of the invention are suitable with preference as additives for rubbers, preferably filled rubbers. More particularly, mixtures of the crosslinked organosilicon polysulphides of the invention with at least one other sulphur-containing organosilicon compound constitute an outstanding additive for silica-containing rubbers, of the kind used for car tyres, for example.

The mixtures of the crosslinked organosilicon polysulphides of the formula (I) of the invention in which the index m is an integer from 1 to 20 with at least one further sulphur-containing organosilicon compound are new and are subject-matter of a parallel patent application filed simultaneously at the European Patent Office.

The mixtures of the crosslinked organosilicon polysulphides of the formula (I) of the invention in which the index m is 0 with at least one further sulphur-containing organosilicon compound are new and are additionally provided by this application.

The mixtures of the invention comprise at least one crosslinked organosilicon polysulphide of the above generally and preferably stated formula (I), and at least one compound of the formula $$R^1R^2R^3Si-X^1-S_x-X^2-SiR^1R^2R^3 \quad (II)$$

in which $R^1$, $R^2$ and $R^3$ independently of one another are alkoxy, preferably $C_1$-$C_6$-alkoxy, more particularly methoxy or ethoxy, $X^1$ and $X^2$ independently of one another are alkylene, preferably $C_1$-$C_6$-alkylene, more particularly $C_2$-$C_3$-alkylene, and x is an integer from 1 to 6, preferably from 1 to 4, more preferably from 2 to 4.

Especially preferred compounds of the formula (II) are the following: bis(triethoxysilylpropyl)tetrasulphane and bis(triethoxysilylpropyl)disulphane.

The compounds of the formula (II) and their use as rubber additives are known—cf. e.g. DE-A-2 255577 and EP-A 1 000 968.

The present application provides mixtures comprising at least one organosilicon polysulphide of the formula (I) indicated above as general and preferred, in which the index m is 0, with at least one further organosilicon compound of the formula (II) indicated generally and preferably above.

The present application further provides mixtures comprising at least one crosslinked organosilicon polysulphide of the formula (I) indicated generally and preferably above and at least one compound of the formula (IIa):

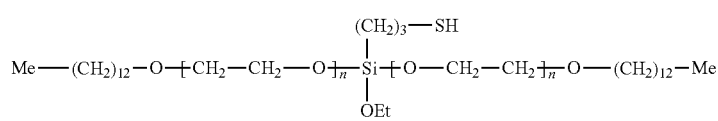

where n is a number from 4 to 6, preferably 5. Me stands for methyl and Et for ethyl.

Additionally provided by the present application are mixtures comprising at least one crosslinked organosilicon polysulphide of the formula (I) indicated generally and preferably above and at least one compound of the formula (IIb):

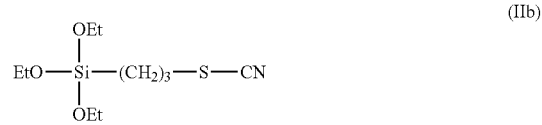

Surprisingly, the crosslinked organosilicon polysulphides of the formula (I) of the invention, especially in a mixture with the compounds of the formula (II), (IIa) or (IIb), as additives, give the vulcanizates produced using them an improved dynamic behaviour, which is manifested, for example, in significantly lower values for the loss factor tan δ (at 60° C.). The tan δ value is an indicator of the rolling resistance of a tyre. A reduction in the tan δ value is therefore manifested in a reduction in the rolling resistance of a car tyre, for example.

By using the crosslinked organosilicon polysulphides of the formula (I) of the invention it is therefore possible to produce more eco-friendly tyres in the sense of the classification planned for 2012 and hence to optimize the "Magic Triangle" of tyre technology. By using the additives of the invention in rubbers it is possible cost-effectively to produce tyres distinguished by reduced running resistance/rolling resistance in combination with good wet grip and long running performance.

A further feature of the crosslinked organosilicon polysulphides of the formula (I) of the invention is that they do not adversely affect the fluidity of the rubber mixtures prepared using them.

The present invention accordingly further provides for the use of the crosslinked organosilicon polysulphides of the formula (I) of the invention, optionally in a mixture with at least one further sulphur-containing organosilicon compound of the formula (II), (IIa) and/or (IIb), as additives for rubbers, more particularly for silica-containing rubbers.

These organosilicon polysulphides of the invention or mixtures of the invention are mixed in a conventional way with the constituents of the rubber mixture.

The additives/mixtures of the invention are added to the rubber mixture in an amount of preferably in each case 0.1 to 15 percent by weight, more particularly from 0.3 to 7 percent by weight, based on the rubber.

The present invention additionally provides silica-containing rubber mixtures comprising an additive of the invention.

The rubber mixtures of the invention comprise at least one rubber, a crosslinker, a filler and optionally other rubber aux The rubber mixtures of the invention can be prepared in a known way by mixing the individual constituents with one another (using, for example, an internal mixer, rolls or extruder). iliaries.

The silica-containing rubber mixture of the invention preferably comprises at least one SBR rubber and at least one BR rubber.

It preferably comprises at least one SBR rubber and at least one BR rubber in an SBR:BR weight ratio of 60:40 to 90:10.

The silica-containing rubber mixture may further comprise at least one NR rubber.

It preferably comprises at least one SBR rubber and at least one BR rubber and at least one NR rubber in a ratio of at least 60 and not more than 85 percent by weight of SBR, based on rubber and at least 10 and not more than 35 percent by weight of BR, based on rubber, and at least 5 and not more than 20 percent by weight of NR, based on rubber.

As well as natural rubber, synthetic rubbers are also suitable for preparing the rubber mixtures of the invention and producing the rubber vulcanizates of the invention. Preferred synthetic rubbers are described for example in W. Hofmann, Kautschuktechnologie, Genter-Verlag, Stuttgart 1980.

They include the following:
BR-polybutadiene
ABR-butadiene/$C_1$-$C_4$-alkyl acrylate copolymer
CR-polychloroprene
IR-polyisoprene
SBR-styrene/butadiene copolymers with styrene contents of 1-60%, preferably 20%-50% by weight
IIR-isobutylene/isoprene copolymers
NBR-butadiene/acrylonitrile copolymers having acrylonitrile contents of 5-60%, preferably 10-50% by weight
HNBR-partially hydrogenated or fully hydrogenated NBR rubber
EPDM-ethylene/propylene/diene copolymers
and also mixtures of these rubbers.

The silica-containing rubber mixtures of the invention contain in general 0.1 to 15 parts by weight of additive of the invention per 100 parts by weight of rubber used. The rubber mixtures of the invention preferably contain 0.3 to 13, more particularly 0.3 to 7 parts by weight of additive of the invention per 100 parts by weight of rubber used.

The rubber mixtures of the invention may comprise organic and/or inorganic fillers, examples being those from the group of the oxidic and silicatic fillers and carbon blacks, with the fillers being employed generally in the range from 50 to 200 parts by weight, preferably 60 to 120 parts by weight, per 100 parts by weight of rubbers used.

The rubber mixtures of the invention preferably comprise at least one filler selected from the group consisting of precipitated silicas and/or silicates having a specific surface area of 20 to 400 m$^2$/g, preferably having a specific surface area of 100 to 200 m$^2$/g.

The additive of the invention has the effect of a reinforcing additive. Thus, for example, preferred rubber mixtures of the invention are notable for the fact that a vulcanizate thereof heated at 170° C./t95 has a loss factor tan δ at 60° C. of <0.2, more particularly of <0.145, and at the same time a Shore A hardness at 23° C. of >65, and also a modulus 300 value of >12 MPa, preferably >15 MPa.

Preferred rubber mixtures of the invention are further notable for the fact that a vulcanizate thereof heated at 170° C./t95 has a loss factor tan δ at 60° C. of less than 0.145 and at the same time a scorch time of greater than 500 seconds.

Preferred rubber mixtures of the invention are further notable for the fact that a vulcanizate thereof heated at 170° C./t95 has a loss factor tan δ at 60° C. of less than 0.145 and at the same time a full vulcanization time of less than 2000 seconds.

In preferred rubber mixtures of the invention, the mixture viscosity ML 1+4 at 100° C. is generally less than 150, more preferably less than 100.

The present invention further provides rubber vulcanizates producible from the rubber mixtures of the invention.

The present invention additionally provides a method for producing filled rubber vulcanizates which is characterized in that
i) at least one rubber is mixed with
ii) 10%-150%, preferably 30%-120% by weight, based on rubber (i), of filler and
iii) in each case 0.1%-15%, preferably in each case 0.3%-7% by weight, based on rubber (i), of organosilicon polysulphide additives of the formula (I) and optionally of the formulae (II), (IIa) and/or (IIb)
at compound temperatures of at least 120° C. and at shear rates of 1-1000 sec (exp.-1), preferably 1-100 sec (exp.-1), and subsequently, following addition of further vulcanizing chemicals, vulcanizing the mixture in a customary way.

The addition of the additive/mixture of the invention and also the addition of any further auxiliaries are made preferably in the first part of the mixing operation at compound temperatures of 100-200° C. under the aforementioned shear rates, hut may also be made later at lower temperatures (40-100° C.) e.g. together with sulphur and accelerator. In this case the additive of the invention may be added directly as a mixture of the components of the formulae (I) and (II), (IIa) and/or (IIb) or in the form of the individual components.

The additive of the invention or its individual components may be added to the mixing operation either in pure form or else adsorbed on inert, organic or inorganic supports. Preferred support materials are silica, natural or synthetic silicates, aluminium oxide and/or carbon black.

Silica-containing fillers in the sense of this invention contemplated for the rubber mixture and rubber vulcanizates of the invention include the following fillers:
finely divided silica, produced for example by precipitation from solutions of silicates or pyrolysis of silicon halides with specific surface areas of 5-1000, preferably 20-400 m$^2$/g (BET surface area) and with primary particle sizes of 10-400 nm. The silicas may optionally also take the form of mixed oxides with other metal oxides such as Al, Mg, Ca, Ba, Zn, Zr and Ti oxides.
synthetic silicates, such as aluminium silicate, alkaline earth metal silicates such as magnesium or calcium silicate, with BET surface areas of 20-400 m$^2$/g and primary particle size of 10-400 nm,
natural silicates, such as kaolin and other naturally occurring silicas,
glass fibres and glass fibre products (mats, strands) or glass microbeads.

As further fillers it is possible to use carbon blacks. The carbon blacks for use in this context are produced for example by the lamp black, furnace black or gas black process and possess BET surface areas of 20-200 m$^2$/g, such as SAF, ISAF, HSAF, HAF, FEF, or GPF blacks.

The additive of the invention is used preferably in amounts of 0.1 to 15%, based on rubber, in the rubber mixtures of the invention.

One particularly preferred variant is the combination of silica, carbon black and additives of the formula (I). With this combination it is possible to vary within any desired limits the ratio of silica to carbon black. From the tyre technology standpoint, a silica:carbon black ratio of 20:1 to 1.5:1 is preferred.

The rubber vulcanizates of the invention may comprise further rubber auxiliaries, such as reaction accelerators, ageing inhibitors, heat stabilizers, light stabilizers, ozone protectants, processing auxiliaries, plasticizers, tackifiers, blowing agents, dyes, pigments, waxes, extenders, organic acids, retardants, metal oxides and also activators, such as triethanolamine, polyethylene glycol and hexanetriol, which are known to the rubber industry.

The rubber auxiliaries are used in customary amounts, which are guided by factors including the intended use of the vulcanizates. Customary amounts are 0.1% to 30% by weight, based on rubber.

Crosslinking agents used are peroxides, sulphur, magnesium oxide, zinc oxide, which may be admixed with the known vulcanization accelerators, such as mercaptobenzothiazoles, mercaptosulphenamides, thiuram, thiocarbamates, guanidines, xanthogenates and thiophosphates. Sulphur is preferred.

The crosslinking agents and vulcanization accelerators are used typically in amounts of about 0.1% to 10% by weight, preferably 0.1% to 5% by weight, based on rubber.

As already mentioned above, it is advantageous to counter the effects of heat and oxygen by adding ageing inhibitors to the rubber mixture. Suitable phenolic ageing inhibitors are alkylated phenols, styrenized phenols, sterically hindered phenols such as 2,6-di-tert-butylphenol, 2,6-di-tert-butyl-p-cresol (BHT), 2,6-di-tert-butyl-4-ethylphenol, sterically hindered phenols containing ester groups, sterically hindered phenols containing thioether, 2,2'-methylenebis(4-methyl-6-tert-butylphenol) (BPH) and also sterically hindered thiobisphenols.

If discoloration of the rubber is unimportant, it is usual also to use aminic ageing inhibitors, examples being mixtures of diaryl-β-phenylenediamines (DTPD), octylated diphenylamine (ODPA), phenyl-α-naphthylamine (PAN), phenyl-β-naphthylamine (PBN), preferably those based on phenylenediamine. Examples of phenylenediamines are N-isopropyl-N'-phenyl-p-phenylenediamine, N-1,3-dimethylbutyl-N'-phenyl-p-phenylenediamine (6PPD), N-1,4-dimethylpentyl-N'-phenyl-p-phenylenediamine (7PPD) and N,N'-bis-1,4-(1,4-dimethylpentyl)-p-phenylenediamine (77PD).

The other ageing inhibitors include phosphites such as tris(nonylphenyl)phosphite, polymerized 2,2,4-trimethyl-1,2-dihydroquinoline (TMQ), 2-mercaptobenzimidazole (MBI), methyl-2-mercaptobenzimidazole (MMBI), zinc methylmercaptobenzimidazole (ZMMBI). The phosphites are used generally in combination with phenolic ageing inhibitors. TMQ, MBI and MMBI are used in particular for NBR types which are vulcanized peroxidically.

The ozone resistance can be enhanced by means of antioxidants which are known to the skilled person, such as, for example, N-1,3-dimethylbutyl-N'-phenyl-p-phenylenediamine (6PPD), N-1,4-dimethylpentyl-N'-phenyl-p-phenylenediamine (7PPD), N,N'-bis-1,4-(1,4-dimethylpentyl)-p-phenylenediamine (77PD), enol ethers or cyclic acetals.

Processing assistants are intended to be effective between the rubber particles and to counter frictional forces in the course of mixing, plastifying and deforming. As processing auxiliaries, the rubber mixture of the invention may comprise all of the lubricants customary for the processing of plastics, such as, for example, hydrocarbons, such as oils, paraffins and PE waxes, fatty alcohols having 6 to 20 C atoms, ketones, carboxylic acids, such as fatty acids and montanic acids, oxidized PE wax, metal salts of carboxylic acids, carboxamides and carboxylic esters, as for example with the alcohols ethanol, fatty alcohols, glycerol, ethanediol and pentaerythritol, and with long-chain carboxylic acids as the acid component.

The rubber mixture may be crosslinked both with sulphur accelerator systems and with peroxides.

Examples of crosslinkers contemplated include peroxidic crosslinkers such as bis(2,4-dichlorobenzoyl)peroxide, dibenzoyl peroxide, bis(4-chlorobenzoyl)peroxide, 1,1-bis(tert-butylperoxy)-3,3,5-trimethylcylohexane, tert-butyl perbenzoate, 2,2-bis(tert-butylperoxy)butene, 4,4-di-tert-butyl peroxynonylvalerate, dicumyl peroxide, 2,5-di methyl-2,5-di(tert-butylperoxy)hexane, tert-butyl cumyl peroxide, 1,3-bis(tert-butylperoxyisopropyl)benzene, di-tert-butyl peroxide and 2,5-dimethyl-2,5-di(tert-butylperoxy)hex-3-yne.

In addition to these peroxidic crosslinkers it may be advantageous to use other additives as well that can be employed in order increase the crosslinking yield: suitable for this purpose, for example, are triallyl isocyanurate, triallyl cyanurate, trimethylolpropane tri(meth)acrylate, triallyl trimellitate, ethylene glycol dimethacrylate, butanediol dimethacrylate, trimethylolpropane trimethacrylate, Zn diacrylate, Zn dimethacrylate, 1,2-polybutadiene or N,N'-m-phenylenedimaleimide.

As crosslinkers it is also possible to use sulphur in elemental soluble or insoluble form or sulphur donors.

Examples of sulphur donors contemplated include dimorpholyl disulphide (DTDM), 2-morpholinodithiobenzothiazole (MBSS), caprolactam disulphide, dipentamethylenethiuram tetrasulphide (DPTT), and tetramethylthiuram disulphide (TMTD).

In the case of sulphur vulcanization of the rubber mixture of the invention as well it is possible to use further additives that can be employed to increase the crosslinking yield. In principle, however, crosslinking may also take place with sulphur or sulphur donors alone.

Examples of suitable additives that can be employed to increase the crosslinking yield include dithiocarbamates, thiurams, thiazoles, sulphenamides, xanthogenates, bicyclic or polycyclic amines, guanidine derivatives, dithiophosphates, caprolactams and thiourea derivatives.

Also suitable as additives are the following, for example: zinc diamine diisocyanate, hexamethylenetetramine, 1,3-bis(citraconimidomethyl)benzene and also cyclic disulphanes.

In the rubber mixture of the invention the sulphur accelerator system is preferred.

In order to reduce flammability and to reduce the smoke given off on burning, the rubber mixture composition of the invention may also comprise flame retardants. Examples of flame retardants used are antimony trioxide, phosphoric esters, chlorinated paraffin, aluminium hydroxide, boron compounds, zinc compounds, molybdenum trioxide, ferrocene, calcium carbonate or magnesium carbonate.

The rubber vulcanizate may also comprise other plastics, which act, for example, as polymeric processing auxiliaries or impact modifiers. These plastics are selected from the group consisting of the homopolymers and copolymers based on ethylene, propylene, butadiene, styrene, vinyl acetate, vinyl chloride, glycidyl acrylate, glycidyl methacrylate, acrylates and methacrylates with alcohol components of branched or unbranched C1 to C10 alcohols. They include, in particular, polyacrylates with identical or different alcohol residues from the group of the C4 to C8 alcohols, more particularly of butanol, hexanol, octanol and 2-ethylhexanol, polymethyl methacrylate, methyl methacrylate-butyl acrylate copolymers, methyl methacrylate-butyl methacrylate copolymers, ethylene-vinyl acetate copolymers, chlorinated polyethylene, ethylene-propylene copolymers and ethylene-propylene-diene copolymers.

The rubber vulcanizate of the invention may be used for example for producing foams. For that purpose it is admixed with chemical or physical blowing agents. Suitable chemical blowing agents include all substances known for this purpose, such as, for example, azodicarbonamide, p-toluenesulphonyl hydrazide, 4,4'-oxybis(benzenesulphohydrazide), p-toluenesulphonylsemicarbazide, 5-phenyltetrazole, N,N'-dinitrosopentamethylenetetramine, zinc carbonate or sodium hydrogencarbonate, and mixtures comprising these substances. Examples of suitable physical blowing agents include carbon dioxide or halogenated hydrocarbons.

The vulcanization may take place for example at temperatures of 100-200° C., preferably 130-180° C., optionally under a pressure of 10-200 bar.

The operations of blending the rubber with the filler and the additives of the invention may be carried out in customary mixing assemblies, such as rolls, internal mixers and mixer-extruders.

The rubber vulcanizates of the invention are suitable for producing mouldings having improved properties, as for example for the production of cable sleeves, hoses, drive belts, conveyor belts, roll linings, tyres, footwear soles, gaskets and damping elements.

Likewise provided by the present invention is a new process for preparing the crosslinked organosilicon polysulphides of the formula (I) of the invention.

Generally speaking, sulphur- and/or silicon-containing compounds can be prepared in a variety of ways. In the industry, silanes are always prepared with solvents and catalysts in the absence of water. It is state of the art to use solvents such as methanol, ethanol, propanol or butanol, which are removed again after the reaction. From the present state of the art it has so far not become known to the skilled person to prepare silanes in an aqueous medium.

From EP-A 0 670 347 it is known that sulphur- and silicon-containing reinforcing additives which contain an alkylene group between the silicon and sulphur can be prepared by reacting silanes containing mercapto groups and dimercaptans and/or polymercaptans with sulphur dichloride or disulphur dichloride, with elimination of HCl. This reaction is carried out in the presence of solvents, such as alcohols or aromatic hydrocarbons.

Known from GB-A 1 102 251 is the reaction of anhydrous alkali metal hydrogensulphides with (haloalkyl)alkoxysilanes in methanolic medium to give the corresponding (mercaptoalkyl)alkoxysilanes under atmospheric pressure, and, from EP-A 0 471164, by reaction with anhydrous alkali hydrogensulphide.

Surprisingly, a new process has been found for preparing organosilicon polysulphides, which is carried out in aqueous medium.

The present invention provides a process for preparing organosilicon polysulphides of the formula (I)

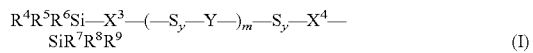

$$R^4R^5R^6Si-X^3-(-S_y-Y-)_m-S_y-X^4-SiR^7R^8R^9 \quad (I)$$

in which the substituents and indices have the definitions stated above for formula (I) as general and preferred, but the index m is an integer from 1 to 20, which process is characterized in that at least one compound of the formula (III)

$$R^4R^5R^6Si-X^3-SH \quad (III)$$

in which $X^3$ is alkylene, $R^4$, $R^5$ and $R^6$ independently of one another are —OH, —Ometal, alkyl, alkoxy, phenyl or phenoxy, where metal is a metal ion from the series of the alkali metals and alkaline earth metals, and at least one compound of the formula (IV)

$$R^7R^8R^9Si-X^4-SH \quad (IV)$$

in which $R^7$, $R^8$ and $R^9$ independently of one another are —OH, —Ometal, alkyl, alkoxy, phenyl or phenoxy, and where metal is a metal ion from the series of the alkali metals and alkaline earth metals, and $X^4$ is alkylene, is reacted with at least one compound of the formula (V)

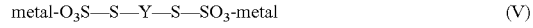

$$\text{metal-}O_3S-S-Y-S-SO_3\text{-metal} \quad (V)$$

in which metal is a metal ion from the series of the alkali metals and alkaline earth metals, and Y is a divalent, optionally substituted, optionally heteroatom-containing aliphatic, cycloaliphatic or aromatic group, in an aqueous or aqueous-organic medium.

The substituents $X^3$, $X^4$, $R^4$, $R^5$, $R^6$, R7, $R^8$ and $R^9$, Y and metal in the formulae (III), (IV) and (V) have preferably and more preferably the same definitions as indicated as being preferred and more preferred for these substituents and metal in formula (I).

The process of the invention is carried out generally at a temperature from 0 to 100 degrees Celsius; the reaction may optionally also take place at temperatures above 100 degrees Celsius under pressure. The reactants of the formulae (III), (IV) and (V) are reacted preferably in the presence of an aldehyde and/or ketone, more particularly in the presence of formaldehyde and/or acetaldehyde and/or acetone and/or methyl ethyl ketone, more preferably in the presence of formaldehyde, in an aqueous or aqueous-organic medium. The reaction preferably takes place under inert gas. The reaction preferably takes place at a pH of 5 to 10.

The degree of crosslinking may be adjusted in particular by means of the reaction parameters of temperature, pH, concentration of the reactants of the formulae (III), (IV) and (V) in the reaction mixture, and the duration of the reaction. Thus, in particular, higher temperatures and longer reaction times lead to greater crosslinking; in other words, the Si(OSi)₃ fraction increases. The degree of crosslinking may be monitored by sampling during the reaction and the $^{29}$Si NMR spectroscopic analysis of the sample. When the desired degree of crosslinking has been reached, further crosslinking may be discontinued by isolating the reaction product by filtration.

The product of the formula (I) is advantageously isolated in solid form and washed with water until electrolyte-free (<500 µS).

Non-crosslinked organosilicon polysulphides which conform to the formula (I), but without the crosslinking via the substituents of the formula (Ia), and in which the index m is 0, are already known from the prior art and can be prepared in a known way. From these known non-crosslinked compounds, it is possible to prepare the organosilicon polysulphides of the formula (I) of the invention, in which the substituents and indices have the definition stated generally and preferably for that formula, and the index m is 0, by reacting the corresponding non-crosslinked compounds with one another in an aqueous or aqueous-organic medium. This reaction may take place at a temperature of 0 to 100 degrees Celsius or else at temperatures above 100 degrees Celsius under pressure.

The degree of crosslinking may be adjusted in particular by means of the reaction parameters of temperature, pH, concentration of the non-crosslinked reactants of the formula (I)

in the reaction mixture, and the duration of the reaction. Thus, in particular, higher temperatures and longer reaction times lead to greater crosslinking; in other words, the Si(OSi)$_3$ fraction increases. The degree of crosslinking may be monitored by sampling during the reaction and the $^{29}$Si NMR spectroscopic analysis of the sample. When the desired degree of crosslinking has been reached, further crosslinking may be discontinued by isolating the reaction product by filtration.

The product of the formula (I) is advantageously isolated in solid form and washed with water until electrolyte-free (<500 µS).

In the text below, the intention is to illustrate the present invention by means of examples, but without restricting this invention to these examples.

BRIEF DESCRIPTION OF THE DRAWING

FIG. 1 shows a $^{29}$Si solid-state NMR spectrum of the inventive organosilicon polysulphide of Example 1, measured under quantitative conditions (direct excitation of the $^{29}$Si nuclei, relaxation delay of 60 s) under sample rotation at the magic angle of 10 kHz.

EXAMPLE 1

Preparation of an Inventive Organosilicon Polysulphide

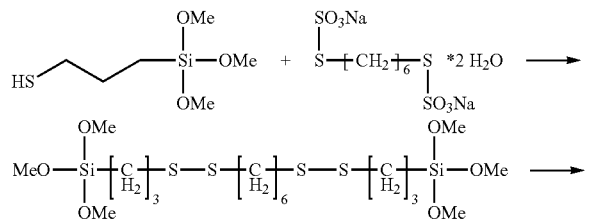

partially hydrolysed product crosslinked by Si—O—Si units.

| Apparatus: | 2000 ml four-necked flask with thermometer, dropping funnel with pressure compensation, reflux condenser with gas diversion fitting (bubble counter) and tube, stirrer with 250 rpm, pH meter | |
|---|---|---|
| Initial charge: | 99.1 g = 0.25 mol | Duralink ® HTS (98.48%; CAS No.: 5719-73-3) |
| | 800 ml | fully demineralized water |
| | 41.1 g = 0.5 mol | formaldehyde solution, 36.5% strength |
| | 42 g = 0.5 mol | sodium hydrogencarbonate |
| | 50 ml | toluene (analytical grade) |
| Feed: | 103.3 g = 0.5 mol | 3-mercaptopropyltrimethoxysilane (≥95%) |

Duralink® HTS and water were introduced as initial charge into the nitrogen-flushed apparatus. The stirrer was switched on and then first sodium hydrogencarbonate and then formaldehyde and subsequently the toluene were added.

Then, at a reaction temperature of 20 to 25° C., the 3-mercaptopropyltrimethoxysilane was added dropwise under nitrogen blanketing over the course of approximately 30 minutes. After the end of the metered feed, stirring was continued at 20 to 25° C. for 22 hours and the solid was subsequently filtered off with suction using a D4 frit. The product was thereafter washed with 6 times 500 ml of fully demineralized water. The product was subsequently dried to constant weight in a vacuum drying cabinet at 25° C.

Yield: 122 g

The inventive product obtained is a partially crosslinked organosilicon polysulphide. The structure of the resulting product was determined by $^{29}$Si solid-state NMR analysis. Table 1 below shows the signal assignment and evaluation of the amount-of-substance fraction/degree of crosslinking.

TABLE 1

Signal assignment and evaluation of the amount-of-substance fraction of Example 1

| Signal position/ppm | Assignment | Amount-of-substance fraction/% |
|---|---|---|
| −67.6 | R—Si—(OSi)$_3$ | 67 |
| −58.8 | R—Si—(OSi)$_2$(OH/OMe) | 22 |
| −50.5 | R—Si—(OSi)$_1$(OH/OMe)$_2$ | 8 |
| −42.3 | R—Si—(OH/OMe)$_3$ | 3 |

*Substance fraction carries a relative error of ±10 percent.

FIG. 1 shows a $^{29}$Si solid-state NMR spectrum of the inventive organosilicon polysulphide of Example 1, measured under quantitative conditions (direct excitation of the $^{29}$Si nuclei, relaxation delay of 60 s) under sample rotation at the magic angle of 10 kHz.

The $^{29}$Si solid-state NMR spectra were recorded with proton decoupling and with direct excitation of the $^{29}$Si nuclei. The measurement was carried out under MAS (magic-angle spinning) with a rotational frequency of 10 kHz. On the basis of the signal position, the signals in the $^{29}$Si spectrum (FIG. 1) were assigned. As a result of direct excitation of the $^{29}$Si nuclei and of an extended recycle delay of 60 s, it is possible to define the relative amount-of-substance fractions of the silicon atoms from the integrals of the signals.

Performance Results:

For the tests, the following rubber formulas were selected as set out in Table 1. All of the numerical figures, unless noted otherwise, relate to "parts per hundred rubber" (phr).

The rubber mixtures below were prepared in a 1.5 l internal mixer (70 rpm), starting temperature 80° C., mixing time: 5 minutes. Sulphur and accelerator were mixed in at the end on a roll (temperature: 50° C.).

TABLE 1

| Rubber formula | | |
|---|---|---|
| | Reference | Example 1 |
| BUNA CB 24 (oil-extended rubber from LANXESS Deutschland GmbH) | 30 | 30 |
| BUNA VSL 5025-1 (LANXESS Deutschland GmbH) | 96 | 96 |
| CORAX N 339 (commercial carbon black) | 6.4 | 6.4 |
| VULKASIL S (precipitated silica from LANXESS Deutschland GmbH) | 80 | 80 |
| TUDALEN 1849-1 (mineral oil) | 8 | 8 |
| EDENOR C 18 98-100 | 1 | 1 |
| VULKANOX 4020/LG | 1 | 1 |
| VULKANOX HS/LG | 1 | 1 |
| ZINC OXIDE RED SEAL | 2.5 | 2.5 |
| ANTILUX 654 | 1.5 | 1.5 |
| Si ® 69 (additive for formula (II)) | 6.4 | 6.4 |

TABLE 1-continued

Rubber formula

|  | Reference | Example 1 |
|---|---|---|
| VULKACIT D/C | 2 | 2 |
| VULKACIT CZ/C | 1.5 | 1.5 |
| GROUND SULPHUR 90/95 CHANCEL | 1.5 | 1.5 |
| Example 1 (additive for formula (I)) |  | 1.0 |

TABLE 2

Compilation of the results

| Parameter | Unit | DIN | Reference | Example 1 |
|---|---|---|---|---|
| Mooney viscosity (ML 1 + 4) | [MU] | 53523 | 91 | 98 |
| Mooney scorch at 130° C. (t5) | sec | ASTM D 5289-95 | 1032 | 668 |
| Full vulcanization at 170° C./t95 | s | 53529 | 1452 | 1534 |
| Shore A hardness at 23° C. | [Shore A] | 53505 | 67 | 66 |
| Modulus 300 | MPa | 53504 | 16 | 16 |
| Elongation at break | % | 53504 | 329 | 308 |
| Tensile strength | MPa | 53504 | 18 | 17 |
| Abrasion | mm³ | 53516 | 87 | 83 |
| Rolling resistance (tan δ (60° C.)) | — |  | 0.152 | 0.135 |
| Wet grip (tan δ (0° C.)) | — |  | 0.383 | 0.421 |

As shown with the results in Table 2, it was surprisingly found that with the inventive additive a loss factor (tan δ at 60° C.) of more than 10 percent lower was measured relative to the reference product. At the same time, the mechanical properties such as tensile strength, elongation at break and modulus 300 remain virtually unchanged. The vulcanizate tested exhibits an improved wet grip compared to the reference (loss factor tan δ at 0° C.>0.40) and also very advantageous abrasion levels (<90 mm³).

Tests of the Rubber Mixture and of the Vulcanizates:

Mooney Viscosity Measurement:

The viscosity can be determined directly from the force with which rubbers (and rubber mixtures) oppose their processing. In the case of the Mooney shearing disc viscometer, a grooved disc is surrounded with sample substance top and bottom and is moved within a heatable chamber at approximately two revolutions per minute. The force needed to achieve this is recorded as the torque and corresponds to the respective viscosity. The sample is generally preheated to 100° C. over the course of one minute; the measurement lasts a further 4 minutes, with the temperature being held constant.

The viscosity is indicated together with the respective test conditions: for example, ML (1+4) 100° C. (Mooney viscosity, large rotor, preheat time and test time in minutes, test temperature).

The viscosities of the rubber mixtures identified in Table 1 are measured using a Mooney shearing disc viscometer.

Scorch Behaviour (Scorch Time t5):

With the same test as described above it is also possible, furthermore, to measure the "scorch" behaviour of a mixture. The temperature selected in this patent is 130° C. The rotor runs until the torque value, after passing through a minimum, has risen to 5 Mooney units relative to the minimum value (t5). The greater the value (the units are seconds), the slower the incipient vulcanization takes place (high scorch values).

Rheometer (Vulcameter) Vulcanization Time 170° C./t95:

The vulcanization profile on the MDR (moving die rheometer) and analytical data thereof are measured on a Monsanto MDR 2000 rheometer in accordance with ASTM D5289-95. The results of this test are compiled in Table 2.

For the full vulcanization time, a measurement is made of the time at which 95% of the rubber is crosslinked. The selected temperature was 170° C.

Determination of Hardness:

To determine the hardness of the inventive rubber mixture, rolled sheets 6 mm thick were produced from the rubber mixture as per the formulas in Table 1. Test specimens with a diameter of 35 mm were cut from the rolled sheets, and their Shore A hardness values were determined using a digital Shore hardness tester (Zwick GmbH & Co. KG, Ulm).

Tensile Test:

The tensile test serves directly to determine the exposure limits of an elastomer. The lengthwise extent at break is related to the initial length and corresponds to the elongation at break. Furthermore, the force when particular stages of elongation are reached—usually 50%, 100%, 200% and 300%—is determined and is expressed as the stress value (tensile strength at the stated elongation of 300%, or modulus 300).

The test results are set out in Table 2.

Dynamic Damping:

Dynamic testing methods are used to characterize the deformation behaviour of elastomers under periodically altered exposures. A stress applied externally changes the conformation of the polymer chain.

In this measurement, the loss factor tan δ is determined indirectly via the ratio between loss modulus G" and storage modulus G'.

What is claimed is:

1. A silica-containing rubber mixture comprising:
a silica-containing rubber; and
a silicon polysulphide additive of the formula (I)

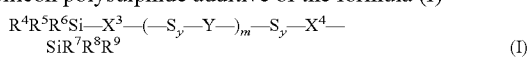
(I)

in which
X$^3$ and X$^4$, independently of one another, are alkylene,
Y is a divalent, aliphatic, cycloaliphatic or aromatic group,
y is an integer from 1 to 6,
m is an integer from 0 to 20, and
R$^4$, R$^5$, R$^6$, R$^7$, R$^8$ and R$^9$, independently of one another, are —OH, —Ometal, alkyl, alkoxy, phenyl or phenoxy, wherein at least one of the substituents R$^4$, R$^5$, R$^6$, R$^7$, R$^8$ and R$^9$ is a radical of the formula

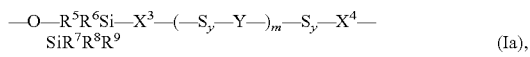
(Ia), and metal is a metal ion from the series of the alkali metals and alkaline earth metals and wherein the silicon polysulphide additive for the formula (I) is added to and mixed with the silica-containing rubber mixture.

2. The silica-containing rubber mixture according to claim 1, wherein, in formula (I)
X$^3$ and X$^4$, independently of one another, are C$_1$-C$_6$-alkylene,
Y is a straight-chain, branched or cyclic C$_1$-C$_{18}$-alkylene radical which is optionally substituted by C$_6$-C$_{12}$-aryl, C$_1$-C$_8$-alkoxy or hydroxyl groups and which is optionally interrupted by oxygen, sulphur or nitrogen atoms or by $C_6$-$C_{12}$-aryl, or is a divalent, optionally substituted, optionally heteroatom-containing aliphatic, cycloaliphatic or aromatic group, y is an integer from 2 to 4, m is an integer from 0 to 6, $R^4$, $R^5$, $R^6$, $R^7$, $R^8$ and $R^9$, independently of one another, are —OH, —Ometal, or $C_1$-$C_8$-alkoxy, and at least one of the substituents $R^4$, $R^5$, $R^6$, $R^7$, $R^8$ and $R^9$ is a radical of the formula

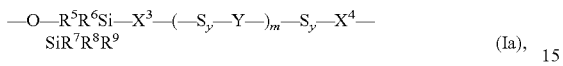 (Ia), and the metal is a metal on selected from the series Na, K, Mg/2 and Ca/2.

3. The silica-containing rubber mixture according to claim 1, wherein in formula (I)

$X^3$ and $X^4$, independently of one another, are $C_2$-$C_3$-alkylene,

Y is a radical of the formula

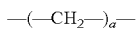

where a=2-12, or

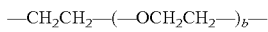

where b=1-4, y is 2, 3 or 4, m is 0, 1, 2, 3, 4, 5 or 6, $R^4$, $R^5$, $R^6$, $R^7$, $R^8$ and $R^9$, independently of one another, are —OH, —ONa, —OK, —O—(Mg/2), —O—(Ca/2), methoxy or ethoxy, and at least one of the substituents $R^4$, $R^5$, $R^6$, $R^7$, $R^8$ and $R^9$ is a radical of the formula

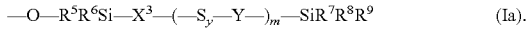 (Ia).

4. The silica-containing rubber mixture according to claim 1, wherein in formula (I)

$X^3$ and $X^4$, independently of one another, are $C_2$-$C_3$-alkylene,

Y is —$(CH_2)_6$—, y is 2, 3 or 4, m is 1, 2, 3, 4, 5 or 6 and $R^4$, $R^5$, $R^6$, $R^7$, $R^8$ and $R^9$, independently of one another, are —OH, —ONa, methoxy or ethoxy and at least one of the substituents $R^4$, $R^5$, $R^6$, $R^7$, $R^8$ and $R^9$ is a radical of the formula

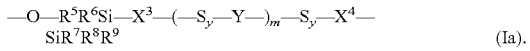 (Ia).

5. The silica-containing rubber mixture according to claim 1, wherein in formula (I)

$X^3$ and $X^4$, independently of one another, are $C_2$-$C_3$-alkylene, y is 2, 3 or 4, m is 0, $R^4$, $R^5$, $R^6$, $R^7$, $R^8$ and $R^9$ independently of one another are —OH, —ONa, methoxy or ethoxy and at least one of the substituents $R^4$, $R^5$, $R^6$, $R^7$, $R^8$ and $R^9$ is a radical of the formula

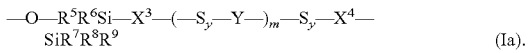 (Ia).

6. The silica-containing rubber mixture according to claim 5, wherein one or more radicals of the formula (Ia) are joined via one or more —Si—O—Si— units to further radicals of the formula (Ia).

7. The silica-containing rubber mixture according to claim 5, further comprising at least one compound of the formula (II)

 (II)

in which $R^1$, $R^2$ and $R^3$, independently of one another, are alkoxy, $X^1$ and $X^2$, independently of one another, are alkylene, and x is an integer from 1 to 6.

8. The silica-containing rubber mixture according to claim 1, wherein the rubber mixture comprises at feast one SBR rubber and at least one BR rubber.

9. The silica-containing rubber mixture according to claim 1, wherein the rubber mixture comprises at least one SBR rubber and at least one BR rubber in an SBR:BR weight ratio of 60:40 to 90:10.

10. The silica-containing rubber mixture according to claim 9, further comprising at least one NR rubber, wherein the rubber comprises at least 60 and not more than 85 percent by weight of SBR, based on total rubber, at least 10 and not more than 35 percent by weight of BR, based on total rubber, and at least 5 and not more than 20 percent by weight of NR, based on rubber.

11. A method for producing vulcanizates and rubber mouldings, the method comprising producing the vulcanizates and rubber mouldings with the silicon-containing rubber mixture according to claim 1.

12. Vulcanizates and rubber mouldings produced by vulcanizing the silicon-containing rubber mixture according to claim 1.

13. The silicon-containing rubber mixture according to claim 1, wherein one or more radicals of the formula (Ia) are joined via one or more —Si—O—Si— units to further radicals of the formula (Ia).

14. The silicon-containing rubber mixture according to claim 4, wherein one or more radicals of the formula (Ia) are joined via one or more —Si—O—Si— units to further radicals of the formula (Ia).

15. A cross-linked silicon polysulphide additive for rubber, the additive comprising compounds of the formula (I)

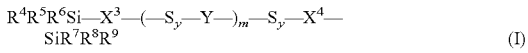 (I)

in which $X^3$ and $X^4$, independently of one another, are alkylene,

Y is a divalent, aliphatic, cycloaliphatic or aromatic group, y is an integer from 1 to 6, m is an integer from 0 to 20, and $R^4, R^5, R^6, R^7, R^8$ and $R^9$, independently of one another, are —OH, —Ometal, alkyl, alkoxy, phenyl or phenoxy, and at least one of the substituents $R^4, R^5, R^6, R^7, R^8$ and $R^9$ is a radical of the formula

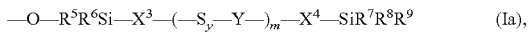
(Ia), and metal is a metal ion from the series of the eke metals and alkaline earth metals; and wherein the compounds of the formula (I) contain in general 0% to 100% by weight of structural units of the formula —Si(Osi—)$_3$;

0% to 50% by weight of structural units of the formula —Si(Osi)$_2$(OX)$_3$;

0% to 30% by weight of structural units of the formula —Si(OSi)$_3$(OX)$_2$; and 0% to 20% by weight of structural units of the formula —Si(OX)$_3$;

where X is H, Na, methyl and/or ethyl and the % by weight add up to 100 percent.

16. The additive according to claim 15, wherein m is 1, 2, 3, 4, 5 or 6.

17. A process for preparing a compound of the formula

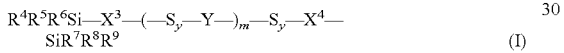
(I)

in which $X^3$ and $X^4$ independently of one another are alkylene,

Y is a divalent, aliphatic, cycloaliphatic or aromatic group, y is an integer from 1 to 6, m is an integer from 0 to 20, and $R^4, R^5, R^6, R^7, R^8$ and $R^9$ independently of one another are —OH, —Ometal, alkyl, alkoxy, phenyl or phenoxy, and at least one of the substituents $R^4, R^5, R^6, R^7, R^8$ and $R^9$ is a radical of the formula

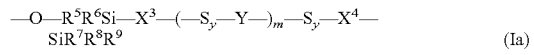
(Ia)

and metal is a metal on from the series of the alkali metals and alkaline earth metals, the process comprising reacting:

at least one compound of the formula (III)

(III)

at least one compound of the formula (IV)

(IV)

at least one compound of the formula (V)

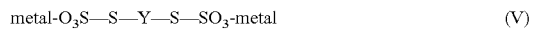
(V)

in an aqueous or aqueous-organic medium.

18. A mixture comprising:

at least one compound of the formula (I)

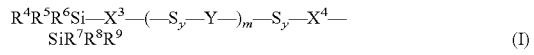
(I)

in which $X^3$ and $X^4$ independently of one another are alkylen,

Y is a divalent, aliphatic, cycloaliphatic or aromatic group, y is an integer from 1 to 6, m is an integer from 0 to 20, and $R^4, R^5, R^6, R^7, R^8$ and $R^9$ independently of one another are —OH, —Ometal, alkyl, alkoxy, phenyl or phenoxy, and at least one of the substituents $R^4, R^5, R^6, R^7, R^8$ and $R^9$ is a radical of the formula

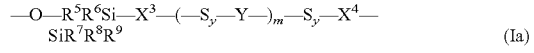
(Ia)

and metal is a metal ion from the series of the alkali metals and alkaline earth metals, and at least one compound of the formula (IIa)

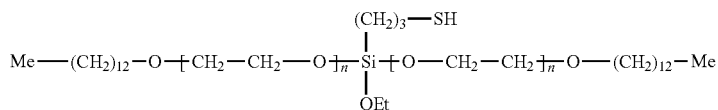

where
n is a number from 4 to 6, and/or
at least one compound of the formula (IIb)
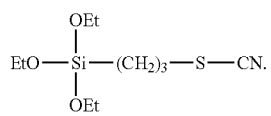
19. A method for producing the silica-containing rubber mixture according to claim 1, the method comprising adding at least one silicon polysulphide additive of the formula (I) as a reinforcing additive to the silica containing rubber mixture.
* * * * *